United States Patent [19]

Nakabayashi et al.

[11] Patent Number: 5,461,433
[45] Date of Patent: Oct. 24, 1995

[54] HIGHLY HYDROUS SOFT CONTACT LENS AND A TREATING SOLUTION FOR CONTACT LENSES

[75] Inventors: Nobuo Nakabayashi, Matsudo; Kazuhiko Ishihara, Kodaira; Yoshishige Murata, Tsukuba; Nobuharu Nakada, Tsukuba; Takeo Matsumoto, Tsukuba; Yasumi Koinuma, Tsukuba, all of Japan

[73] Assignee: NOF Corporation, Tokyo, Japan

[21] Appl. No.: 290,099

[22] Filed: Aug. 15, 1994

Related U.S. Application Data

[63] Continuation of Ser. No. 960,684, Oct. 14, 1992.

[30] Foreign Application Priority Data

Oct. 14, 1991 [JP] Japan .................................. 3-291939
Oct. 14, 1991 [JP] Japan .................................. 3-291940

[51] Int. Cl.$^6$ .......................... G02C 13/00; B08B 11/00; C08F 230/02; C08K 5/05
[52] U.S. Cl. .......................... 351/177; 523/106; 524/388; 524/547; 526/277; 525/937; 252/174.23
[58] Field of Search .......................... 523/106; 524/547, 524/388; 526/277; 525/937; 351/177; 252/174.23

[56] References Cited

U.S. PATENT DOCUMENTS

| | | | |
|---|---|---|---|
| 3,964,832 | 6/1976 | Cohen et al. .......................... | 524/398 |
| 4,067,839 | 1/1978 | Schultz .......................... | 523/108 |
| 4,329,266 | 5/1982 | Suzuki et al. .......................... | 524/376 |

FOREIGN PATENT DOCUMENTS

| | | | |
|---|---|---|---|
| 3039309 | 2/1991 | Japan .......................... | 526/277 |

OTHER PUBLICATIONS

*The Merck Index*, Merck & Co., Inc., pp. 234–235 (1968).

*Primary Examiner*—Andrew E. C. Merriam
*Attorney, Agent, or Firm*—Antonelli, Terry, Stout & Kraus

[57] ABSTRACT

A highly hydrous soft contact lens comprising a copolymer which contains as an ingredient a monomer having constitution similar to that of phospholipid represented by the following general formula:

$$X-(Y)_n-O-\overset{O}{\underset{|}{\overset{\|}{P}}}-O-(CH_2)_2-\overset{R_2}{\underset{R_4}{\overset{|}{N^+}}}-R_3 \quad (1)$$
$$\phantom{X-(Y)_n-O-}O_-$$

wherein X is $CH_2=\underset{R_1}{\overset{|}{C}}-CH_2-O$, $CH_2=\underset{R_1}{\overset{|}{C}}-CH_2-O-\underset{}{\overset{\|}{\underset{O}{C}}}-$, $CH_2=\underset{R_1}{\overset{|}{C}}-O-\underset{O}{\overset{\|}{C}}-$, $CH_2=\underset{R_1}{\overset{|}{C}}-O-$, $CH_2=\underset{R_1}{\overset{|}{C}}-\underset{O}{\overset{\|}{C}}-O-$, $CH_2=\underset{R_1}{\overset{|}{C}}-\underset{O}{\overset{\|}{C}}-NH-$, $CH_2=\underset{R_1}{\overset{|}{C}}-CH_2-O-\underset{O}{\overset{\|}{C}}-NH-$, $CH_2=\underset{R_1}{\overset{|}{C}}-C_6H_4-CH_2-$, $CH_2=\underset{R_1}{\overset{|}{C}}-C_6H_4-O-$, $CH_2=\underset{R_1}{\overset{|}{C}}-C_6H_4-\underset{O}{\overset{\|}{C}}-O-$, and $R_1$ is hydrogen or methyl, Y is $-CH_2-$, $-CH_2-O-$, $-CH_2CH_2-O-$, $-CH_2CH_2CH_2-O-$, $-\underset{CH_3}{\overset{|}{CH}}CH_2-O-$, or $-CH_2CH_2CH_2CH_2-O-$, n is an integer of 1–20, and, $R_2$, $R_3$ and $R_4$ are the same or different groups and alkyl or hydroxyalkyl of 1–8 carbon atoms.

Further, a treating solution for contact lenses which comprises a polymer containing as an ingredient the above monomer and a solvent which can dissolve the polymer.

5 Claims, No Drawings

HIGHLY HYDROUS SOFT CONTACT LENS AND A TREATING SOLUTION FOR CONTACT LENSES

This application is a continuation application of application Ser. No. 960,684, filed Oct. 14, 1992.

BACKGROUND OF THE INVENTION

1. Field of the Invention

The present invention relates to a highly hydrous soft contact lens which has high water content and good transparency and is able to prevent stain adhesion.

Further the present invention relates to a treating solution for contact lenses, more particularly, to a treating solution contact lenses such as a hard contact lens, an anhydrous soft contact lens and a hydrous soft contact lens to give stain resistance and hydrophilic nature to these lenses.

2. Description of the Prior Art

The highly hydrous soft contact lens is characterized in that it gives little feeling of physical disorder to eyeballs in comparison with a hard contact lens not containing water which essentially comprises a monomer such as methyl methacrylate, and siloxanylalkyl methacrylate (Japanese Patent Publication Sho 52-33502 (1977)). As for a hydrous contact lens, a lens essentially containing 2-hydroxyethyl methacrylate supplies little oxygen and gives feeling of physical disorder to eyeballs. Recently, to increase the percentage of water content, a contact lens comprising a copolymer of N-vinyl-pyrrolidone and methyl methacrylate, 2-hydroxyethyl methacrylate or methacrylic acid was proposed, However, the above contact lens has disadvantage that stains are easily adhered to the lens to lower the strength and the lens grows yellowish by repeated heat treatment for sterilization.

Conventionally used contact lenses may be classified into two groups, anhydrous hard or soft contact lenses and hydrous soft contact lenses.

These anhydrous lenses having advantages over the hydrous lenses in terms of stability of materials and simple care are lenses principally containing methyl-methacrylate or lenses made of silicone rubber. Lately, a hard contact lens having high oxygen permeability principally containing silyl type methacrylate or fluoric type methacrylate which gives moderate effects to eyes has been used.

However, the anhydrous lenses have problems that the hydrophobic surface gives feeling of physical disorder to eyeballs and has bad influence on the cells in the eyeballs. In particular, the lenses having high oxygen permeability and containing silicone or fluorine in large quantities are highly hydrophobic, and there are problems of feeling of physical disorder, lowering of adhesion properties and staining of proteins and lipids. Therefore, to change the hydrophobic surface into a hydrophilic surface, it is known to treat with plasma or chemically treat with acid or basic materials. These methods have problems in the maintenance of the hydrophilic nature, the denaturation after the treatment, and troublesome treating steps. As the other method, for example, there is a method disclosed by Japanese Patent Publication No. 48-37910 (1973) in which a contact lens is immersed into a solution containing a water-soluble polymer of polyvinyl alcohol, hydroxyethyl cellulose, polyvinylpyrrolidone or the like. There are disadvantages that hydrophilic contact lenses are not always obtained by the method and the method is not effective for prevention of stains such as proteins and lipids.

In the other hand, the hydrous soft contact lenses give good fitness to eyes and have no problems. However, these lenses are hydrogel lenses principally constituting 2-hydroxyethyl methacrylate, vinylpyrrolidone or the like, and there are disadvantages of adhesion of proteins, lipids and the like to the lenses, and increase of bacteria for sanitary reasons, and lowered mechanical strength for increased water content. Therefore, sanitary care is commonly required for the lenses by boiling, sterilization or by using a care product such as germicides or detergent liquids.

SUMMARY OF THE INVENTION

An object of the present invention is to provide a highly hydrous soft contact lens which has high water content of 40% and more, good mechanical strength, good stain resistance and possibility of long term fitting.

Another object of the present invention is to provide a treating solution for a contact lens, the solution being capable of giving surface hydrophilic nature to anhydrous contact lenses or high water content to hydrous contact lenses, improving the fitness or feeling to eyes, and preventing the adhesion or deposit of stains of proteins and lipids.

The present invention is a highly hydrous soft contact lens comprising a copolymer which contains as an ingredient a monomer having constitution similar to that of phospholipid represented by the following general formula:

$$X-(Y)_n-O-\overset{\overset{O}{\|}}{\underset{\underset{O^-}{|}}{P}}-O-(CH_2)_2-\overset{\overset{R_2}{|}}{\underset{\underset{R_4}{|}}{N^+}}-R_3 \quad (1)$$

wherein X is 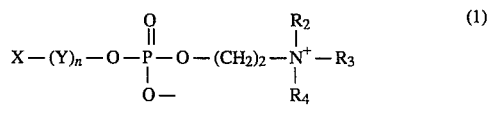

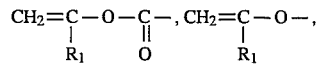

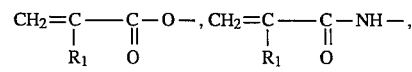

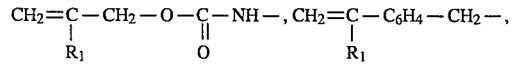

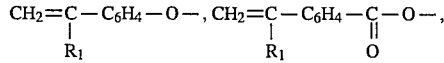

and $R_1$ is hydrogen or methyl, Y is $-CH_2-$, $-CH_2-O$, $-CH_2CH_2-O-$, $-CH_2CH_2CH_2-O-$, $-\underset{\underset{CH_3}{|}}{C}HCH_2-O-$, or $-CH_2CH_2CH_2CH_2-O-$, n is an integer of 1–20, and, $R_2$, $R_3$ and $R_4$ are the same or different groups and alkyl or hydroxyalkyl of 1–8 carbon atoms.

Further, the present invention is a treating solution for contact lenses which comprises a polymer containing is an ingredient the above monomer and a solvent which can dissolve the polymer.

The present invention is embodied in the following.

In the present invention, the monomer having phospholipid-like constitution which is used as an essential ingredient is a monomer represented by the above general formula (1).

In the formula, n is an integer of 1–20. If n is more than 20, the hydrophilic nature of the polymer is undesirably lowered. Carbon atoms of alkyl groups of $R_2$–$R_4$ are 1–8. If the carbon atoms are more than 8, a significant decrease of the hydrophilic nature of the polymer or polymerizability of the monomer is observed, so that such a compound is unsuitable for the use.

As the monomer represented by the above general formula (1), 2-(methacryloyloxy)ethyl 2'-(trimethylammonio)ethyl phosphate, 3-(methacryloyloxy)propyl 2'-(trimethylammonio)ethyl phosphate, 4-(methacryloyloxy)butyl 2'-(trimethylammonio)ethyl phosphate, 5-(methacryloyloxy)pentyl 2'-(trimethylammonio) ethyl phosphate, 6-(methacryloyloxy)ethyl 2'-(trimethylammonio)ethyl phosphate, 2-(methacryloyloxy)ethyl 2'-( N-methyl -N,N-diethylammonio)ethyl phosphate, 2-(methacryloyloxy)ethyl 2'-(N,N-dimethylethylammonio)ethyl phosphate, 2- (methacryloyloxy)ethyl 2'-(triethylammonio)ethyl phosphate, 2-(methacryloyloxy)ethyl 2'-(N,N-dimethylpropylammonio)ethyl phosphate, 2-(methacryloyloxy)ethyl 2'-(N,N-dipropyl-N-methylammonio)ethyl phosphate, 2-(methacryloyloxy) ethyl 2'-(tributylammonio)ethyl phosphate, 2-(methacryloyloxy)ethyl 2'-(tricyclohexylammonio) ethyl phosphate, 2-(vinyloxy)ethyl 2'-(trimethylammonio)ethyl phosphate, 2-(allyloxy) 2'-(trimethylammonio)ethyl phosphate, 2-(p-vinylbenzyl)ethyl 2'-(trimethylammonio) ethyl phosphate, 2- (vinylbenzoyloxy)ethyl 2'-(trimethylammonio)ethyl phosphate, 2-(styryloxy)ethyl 2'-(trimethylammonio)ethyl phosphate, 2-(allyloxycarbonyl)ethyl 2'-(trimethylammonio)ethyl phosphate, 2-(vinyloxycarbonyl)ethyl 2'-(trimethylammonio)ethyl phosphate, 2-(acryloylamino)ethyl 2'-(trimethylammonio)ethyl phosphate, 2-(allyloxycarbonylamino)ethyl 2'-(trimethylammonio)ethyl phosphate, (methacryloyloxy)methyloxy 2'-(trimethylammonio)ethyl phosphate, 2-(methacryloyloxy)ethyloxy 2'-(trimethylammonio)ethyl phosphate, 3-(methacryloyloxy)propyloxy 2'-(tri-methyiammonio)ethyl phosphate, 2-(methacryloyloxy)isomropyloxy 2'-(trimethylammonio)ethyl phosphate, and 4-(methacryloyloxy)butyloxy 2'-(trimethylammonio)ethyl phosphate are exemplified.

Moreover, 2-(methacryloyloxy)propyl 2'-(trimethylammonio)ethyl phosphate, 2-(methacryloyloxy)butyl 2'-(trimethylammonio)ethyl phosphate, 2-(methacryloyloxy)pentyl 2'-(trimethylammonio)ethyl phosphate, 2-(methacryloyloxy)hexyl 2'-(trimethylammonio)ethyl phosphate, 2-(methacryloyloxy)ethyl 2'-(triphenylammonio)ethyl phosphate, 2-(methacryloyoxy)ethyl 2'-(trimethylammonio)ethyl phosphate, 2-(vinyloxy)ethyl 2'-(trimethylammonio)ethyl phosphate, 2-(allyloxy)ethyl 2'-(trimethylammonio)ethyl 2'-(trimethylammonio)ethyl phosphate, 2-(p-vinylbenzyl)oxy 2'-(trimethylammonio)ethyl phosphate, 2-(p-vinylbenzoyloxy)ethyl 2'-(trimethylammonio)ethyl phosphate, 2-(p-vinylbenzyl)ethyl 2'-(trimethylammonio)ethyl phosphate can be exemplified.

These compounds can be used alone or two or more mixtures. The polymers obtained have water solubility and hydrophilic nature. High water content, good stain resistance and good mechanical strength can be given to the contact lens obtained. When the polymers are used in the treating solution for contact lenses of the present invention, such compounds adhere or deposit on the surface of contact lenses, and the contact lenses become hydrophilic and prevent stain adhesion.

The (meth)acrylates represented by the formula (1) which are characteristically used in the present invention can be synthesized by several kinds of commonly known methods. For example, hydroxyalkyl (meth)acrylate is reacted with 2-chloro-2-oxo-1,3,2,-dioxaphosphorane in the presence of amine, the obtained (2-oxo-1,3,2,-dioxaphosphoroyloxy-)alkyl (meth)acrylate is reacted with a certain tertiary amine. In the other method, hydroxyalkyl (meth)acrylate is reacted with 2-bromoethylphosphoryl dichloride, and the obtained (meth)acryloyloxyalkyl 2'-bromoethyl phosphate is reacted with a certain tertiary amine. Before the polymerization, it is desired to purify the products by a known method such as recrystalization.

Preparation of the Contact Lens of the Present Invention

In the preparation of the contact lens, in addition to the above monomers, styrene, α-methylstyrene, nucleus methylated styrene, nucleus chlorinated styrene, vinyl acetate, vinyl propionate, methyl (meth)acrylate, ethyl (meth)acrylate, n-butyl (meth)acrylate, (meth)acrylic acid, (meth)acrylamide, N,N-dimethyl (meth)acrylamide, 2-hydroxyethyl (meth)acrylate, ethylvinyl ether, n-butyl-vinyl ether, N-vinylpyrrolidone, vinylpyridine, diethyl itaconate, and di-n-butyl itaconate can be exemplified as copolymerizable monomers which can be used as starting monomers.

Moreover, polyfunctional monomers such as allyl (meth)acrylate, ethyleneglycol di (meth)acrylate, diethyleneglycol di(meth)acrylate, tetraethylene glycol di(meth)acrylate, 1,4-butanediol di(meth)acrylate, dilyl phthalate, diethylene glycol bisallyl carbonate, divinyl benzene, methylene bisacrylamide, tri-allyl trimellitate and tri-allyl cyanulate can be used.

The monomer ingredient represented by the general formula (1) can be used alone or as a mixture. To increase the heat resistance, processing characteristics and form stability of the highly hydrous soft contact lens obtained, at least one kind of polyfunctional monomers is preferably used. In that case, above-mentioned other copolymerizable monomer can preferably be used at a proportion of 10000 to 5 parts by weight per 100 parts by weight of the monomer (1) having phospholipid-like constitution, especially preferably 1000 to 100 parts by weight. If above-mentioned other monomer ingredient is more than 10000 parts by weight, the water content and stain resistance of obtained hydrous soft contact lens are lowered. If the ingredient is less than 5 parts by weight, the processing characteristics and form stability are lowered.

In the present invention, the contact lens can easily be obtained by radical polymerization of the above starting monomer in the presence of a radical polymerization initiator. As the radical polymerization initiator, a heat polymerization initiator such as benzoyl peroxide, lauroyl peroxide, diisopropyloxy dicarbonate, t-butylperoxypivalate-t-butylperoxy diisobutylate, azobisisobutyronitrile, azobis-2, 4-dimethylvaleronitrile or the like, or a photopolymerization initiator such as benzoinmethyl ether, benzoinethyl ether or the like can preferably be used. The usage of the radical polymerization initiators is preferably 10 or less parts by weight per 100 parts by weight of the starting monomer, more preferably 5 or less parts by weight.

The radical polymerization is conducted by replacing the polymerization atmosphere with an inert gas such as nitrogen, carbon dioxide, helium or the like. In the case of heat polymerization, the polymerization conditions are a temperature of 20°–140° C. and a reaction time of about 6–120 hours. in the case of photopolymerization, ultraviolet light or visual light may be irradiated for one minutes to 20 hours. When necessary, the heat polymerization may be conducted by the photopolymerization.

Further, in the present invention, when necessary, a coloring agent such as pigments, an additive such as ultraviolet absorbinc agents and the like may be added to the starting monomer.

To prepare the hydrous contact lens of the present invention, using the radical polymerization conditions, for example, in one method, the starting monomer is copolymerized in a suitable vessel such as a test tube and obtained rods or blocks are machined by grinding, abrasion or the like. In another method, the starting monomer and the polymerization initiator are injected into a desired form to directly obtain a contact lens by mold polymerization. In the other methods, the starting materials are casted by heat or irradiation, or, after a polymer is previously produced by a radical polymerization method, the polymer is dissolved in a suitable solvent and the solvent is removed by a cast method.

The water content of the highly hydrous soft contact lens of the present invention is 30% or more, preferably 60% or more. If the water content is less than 30%, it has a undesirable influence upon the cornea.

The highly hydrous soft contact lens of the present invention is obtained by polymerization of starting monomers which contain monomers having specified constitution of phospholipid-like constitution, and it has high water content and give physiologically enough oxygen to the cornea and has good stain resistance against the adhesion of protein, lipid and the like.

Preparation of the Treating Solution for Contact Lenses

To prepare the treating solution of contact lenses of the present invention, the polymer used in the treating solution for contact lenses can be obtained by polymerization of (meth)acrylic monomers represented by the formula (1), and also by copolymerization of the monomers with the other copolymerizable vinyl monomers.

As such copolymerizable vinyl monomers, styrene, methylstyrene, chloromethylstyrene, methyl (meth)acrylate, ethyl (meth)acrylate, n-butyl (meth)acrylate, (meth)acrylic acid, (meth)acrylamide, 2-hydroxyethyl (meth)acrylate, ethyl vinyl ether, n-butyl vinyl ether, N-vinyl pyrrolidone, vinyl chloride, vinylidene chloride, ethylene, propylene, isobutylene, acrylonitrile, or mixtures of these compounds can be exemplified. These monomers are preferably used at a proportion of 10000 to 5 parts by weight per 100 parts by weight of the (meth)acrylate (1). If the monomer is more than 10000 parts by weight, sufficient water solubility and stain resistance given by the (meth)acrylic monomer (1) is not observed. If the monomer is less than 5 parts by weight, the polymerization effects are not observed.

The polymers which are characteristically used in the present invention can be obtained by the polymerization or copolymerization of the above monomers. In this case, the polymerization is effected in the presence of a radical polymerization initiator, by a radical polymerization method such as publicly known block polymerization, suspension polymerization, emulsion polymerization, solution polymerization and the like. As the radical polymerization initiator, benzoyl peroxide, lauroyl peroxide, diisopropyloxy dicarbonate, t-butylperoxy-2-ethylhexanoate, t-butylperoxy pivalate, t-peroxydiisobutylate, azobisisobutylonitrile, azobis-dimethylvaleronitrile, persulfate, and persulfate-bisulfite types can be used. The usage of the polymerization initiators is 0.01 to 10 parts by weight per 100 parts by weight of the total amount of monomers, preferably 0.1 to 5 parts by weight.

The polymerization or copolymerization is conducted by replacing the polymerization atmosphere with an inert gas such as nitrogen, carbon dioxide, helium or the like. The polymerization conditions are a temperature of 30°–100° C. for 5–72 hours. The molecular weight of the polymer, which is obtained by the radical polymerization and used in the treating solution for contact lenses of the present invention, can be changed by the polymerization temperature, the usage of the initiator and the presence or absence of a polymerization regulator. The number-average molecular weight of the polymer obtained is 1000 to 300,000 and preferably 2000 to 200,000 in consideration of the solubility in the treating solution, viscosity of the treating solution and adhesion of the solution to contact lenses.

As a solvent used in the treating solution for contact lenses of the present invention, it can be used on conditions that the solvent can dissolve the above polymers and is harmless to contact lenses, and it is usable by simple operation such as immersion, washing, or mixing with water. For example, water, methanol, isopropanol, ethylene glycol, polyethylene glycol, glycerine, ethylene glycol monomethyl ether, dimethyl sulfoxide, tetrahydrofuran, acetone and mixtures of these solvents are exemplified. The polymer concentration in the solvent is 0.01 to 10 parts by weight. When the polymer concentration is less than 0.01 parts by weight, the solvent insufficiently exerts its effect.

When contact lenses are treated by the solution, the contact lenses are immersed in the solution or contacted with the solution at a temperature of 20° to 70° C., and then washed with water, physiological saline or a suitable washing liquid before the use. Accordingly, the contact lenses become hydrophilic, and they are prevented from stains of proteins and lipids.

The treating solution for contact lenses of the present invention can, if necessary, be used with a surfactant, a germicide, an antiseptic and the like, or it can be used as washing liquid or storage liquid.

When the treating solution for contact lenses of the present invention is used, a phospholipid polar polymer adheres to the lenses by simple steps of immersion or coating by the solution and rinse with water. in result, the hydrophilic nature and water content of the surface of anhydrous contact lenses or hydrous soft contact lenses are improved and the fitness to eyes is improved. Furthermore, adhesion and deposit of stains such as proteins and lipids can be controlled, so that the denaturation of the lenses can be prevented and the safety to eyes can be improved.

DESCRIPTION OF THE PREFERRED EMBODIMENT

The following examples illustrate the present invention more specifically. However, the present invention is not limited by these examples.

Highly Hydrous Soft Contact Lenses

EXAMPLE 1

Starting monomers as shown in Table 1, namely, 20 parts by weight of 2-(methacryloyloxy)ethyl 2'-(trimethylammonio)ethyl phosphate, 80 parts by weight of 2-hydroxyethyl methacrylate, 2 parts by weight of allyl me thacrylate, 0.2 parts by weight of azobisisobutyronitrile were injected into a test tube-like glass form. After repeating replacement with nitrogen and degassing in the form, the form was sealed and the materials were heated and polymerized. The heat was effected by a rise in temperature of 50°–100° C. for 50 hours in a thermostat. After finishing the polymerization, transparent colorless polymer was taken out of the form. Obtained polymer was machined by conventional grinding and abrasion to form the desired test film pieces. The following physical properties were evaluated. The results are shown in Table 2.

(1) Water content

After the product film was immersed in 0.9% by weight of physiologic saline and saturated with the saline, the product film was weighed and the water content was determined by the following equation.

$$\text{Water content (\% by weight)} = \frac{(W_1 - W_2)}{W_1} \times 100$$

$W_1$: weight of saturated conditions
$W_2$: initial weight of a film piece (2) Oxygen permeability Oxygen permeability was determined at 35° C. in 0.9% by weight of physiologic saline by using a Seikaken's measuring equipment of film oxygen permeability.

(3) Tensile strength

The test pieces which were an array type of plates having a constricted center were immersed in 0.9% by weight of physiologic saline at 20° C. to be saturated with water, and then these pieces were tested at a stress rate of 60 mm/min.

(4) Stain resistance

After a contact lens is immersed for two weeks at 35° C. in a physiologic saline solution of 0.39% (w/v) of albumin, 0.17% (w/v) of lysozyme and 0.105% (w/v) of γ-globulin, the contact lens was washed with physiologic saline to separate proteins adhered to the contact lens, and a reagent which was quantifiable the proteins was injected into the wash water to determine the amount of the proteins.

EXAMPLES 2–10

Using the same method as used in Example 1, starting monomers as shown in Table 1 were polymerized and the physical properties were determined. The results are shown in Table 2.

COMPARISON EXAMPLES 1–3

Using the same method as used in Example 1, starting monomers as shown in Table 1 were polymerized and the physical properties were determined. The results are shown in Table 2.

TABLE 1

| | starting monomers | (ratio by weight) |
| --- | --- | --- |
| Example 1 | HEMA/METMAEP/DEGMA | (80/20/2) |
| Example 2 | HEMA/METMAEP/DEGMA | (60/40/2) |
| Example 3 | HEMA/METMAEP/AMA | (80/20/2) |
| Example 4 | HEMA/METMAEP/DEGMA | (80/20/2) |
| Example 5 | HEMA/METMAEP/AMA | (80/20/2) |
| Example 6 | HEMA/MMA/METMAEP/DEGMA | (70/10/20/2) |
| Example 7 | HEMA/NVP/METMAEP/DEGMA | (70/10/20/2) |
| Example 8 | NVP/METMAEP/DEGMA | (70/30/2) |
| Example 9 | HEMA/METEAEP/DEGMA | (80/20/2) |
| Example 10 | HEMA/MMA/METEAEP/DEGMA | (70/10/20/2) |
| Comparison example 1 | HEMA/DEGMA | (100/2) |
| Comparison example 2 | HEMA/NVP/DEGMA | (80/20/2) |
| Comparison example 3 | NVP/MMA/AMA | (70/30/2) |

In the table, abbreviations are as follows.

HEMA: 2-hydroxymethyl methacrylate
METMAEP: 2-(methacryloyloxy)ethyl 2'-(trimethylammonio)ethyl phosphate
DEGMA: diethyleneglycol dimethacrylate
AMA: allyl methacrylate
MMA: methyl methacrylate
METMAEP: 3-(methacryloyloxy)propyl 2'-(trimethylammonio)ethyl phosphate
METEAEP: 2-(methacryloyloxy)ethyl 2'-(triethylammonio)ethyl phosphate
NVP: N-vinylpyrrolidone

TABLE 2

| | Water Content (%) | Oxygen Permeability (*) | Tensil Strength (g/mm$^2$) | Stain Resistance (μg/cm$^2$) |
| --- | --- | --- | --- | --- |
| Example 1 | 70 | 22 | 220 | 3.7 |
| Example 2 | 76 | 18 | 202 | 2.9 |
| Example 3 | 68 | 22 | 231 | 2.8 |
| Example 4 | 71 | 21 | 238 | 3.0 |
| Example 5 | 66 | 19 | 256 | 3.9 |
| Example 6 | 52 | 18 | 258 | 2.6 |
| Example 7 | 65 | 21 | 239 | 4.7 |
| Example 8 | 78 | 13 | 169 | 4.3 |
| Example 9 | 74 | 17 | 212 | 2.1 |
| Example 10 | 51 | 20 | 207 | 2.9 |
| Comparison example 1 | 36 | 15 | 210 | 5.5 |
| Comparison example 2 | 41 | 17 | 156 | 11.2 |
| Comparison example 3 | 65 | 26 | 92 | 12.3 |

(*) × $10^{-11}$ ml (STP) cm/cm$^2$ sec mmHg

Treating Solutions for Contact Lenses

PREPARATION EXAMPLE 1

Starting monomers, namely 40 parts by weight of 2-(methacryloyloxy)ethyl 2'-(trimethylammonio)ethyl phosphate, 60 parts by weight of n-butyl methacrylate and 0.1 parts by weight of azobisisobutylonitrile were dissolved in 300 parts by weight of ethanol/tetrahydrofuran (a 50/50 mixture), and the mixture solution was charged into a glass tube. After the atmosphere was replaced with nitrogen, the glass tube was hermetically sealed and heated at a temperature of 60° C. for 12 hours in a thermostatic chamber.

After polymerization, the product was diluted with 50 ml of ethanol, the solution was added to one liter of diethyl ether to preciptate a polymer.

Then, the polymer obtained by suction filtration was dried under reduced pressure at room temperature for 12 hours.

The polymer was dissolved in ethylene glycol to prepare a treating solution for contact lenses.

PREPARATION EXAMPLE 2

Using the same method as described in Preparation example 1 except that 40 parts by weight of 2-(methacryloyloxy)ethyl 2'-(trimethylammonio)ethyl phosphate and 60 parts by weight of 2-hydroxyethyl methacrylate as monomers and 300 parts by weight of ethanol as a solvent were used, a treating solution for contact lenses was prepared.

PREPARATION EXAMPLE 3

Using the same method as described in Preparation example 1 except that 90 parts by weight of 2-(methacryloyloxy)ethyl 2'-(trimethylammonio) ethyl phosphate and 10 parts by weight of styrene as monomers and 300 parts by weight of ethanol as a solvent were used, a treating solution for contact lenses was prepared.

EXAMPLE 11

A common contact lens was prepared by the following method. Starting monomers, namely 99 parts by weight of methyl methacrylate, one part by weight of diethyleneglycol dimethacrylate and 0.2 parts by weight of azobisisobutylonitrile were injected into a test tube-like glass form, and the atmosphere was replaced with nitrogen and degasseal by repetition. After sealing the form, the compounds were heated at a temperature of 50° to 100° C. for 50 hours in a thermostatic chamber. After polymerization, a colorless and transparent polymer was taken out of the form. The polymer obtained was cut and abraded to obtain desired test pieces.

The pieces and a holder were immersed in the solution obtained in Reference example 1 which was charged into a stock case for contact lenses. The pieces and the holder were taken out of the case and thoroughly washed with tap water to obtain hydrophilic contact lenses. Then, the following physical properties were determined. The results are shown in Table 3.

EXAMPLE 12

An oxygen-permeable hard contact lens was prepared by the following method.

The same procedure as in Example 11 was repeated except that the monomers were changed to 40 parts by weight of tris(trimethylsiloxy) silylpropyl methacrylate, 30 parts by weight of trifluoroethyl methacrylate, 10 parts by weight of methyl methacrylate, 15 parts by weight of triethyleneglycol dimethacrylate and 5 parts by weight of methacrylic acid. The contact lens obtained was subjected to hydrophilicity treatment. Then, the following physical properties were determined. The results are shown in Table 3.

EXAMPLE 13

A soft contact lens was prepared. The same procedure as in Example 11 was repeated except that the monomers were changed to 99 parts by weight of 2-hydroxyethyl methacrylate and one part by weight of ethyleneglycol dimethacrylate. Then, the contact lens obtained was subjected to hydrophilicity treatment. Then, the following physical properties were determined. The results are shown in Table 3.

EXAMPLES 14–16

Using the same method as used in Example 11, each hydrophilic contact lens was obtained except that the solution of Preparation example 2 was used. Then, the following physical properties were determined. The results are shown in Table 3.

EXAMPLE 17–19

Using the same method as used in Example 11, each hydrophilic contact lens was obtained except that the solution of Preparation example 3 was used. Then, the following physical properties were determined. The results are shown in Table 3.

COMPARISON EXAMPLE 4

Using the same method as used in Example 11, a hydrophilic contact lens was obtained except that an aqueous solution of polyvinyl alcohol (saponification rate: about 88%) was used. Then, the following physical properties were determined. The results are shown in Table 3.

COMPARISON EXAMPLE 5

Using the same contact lens as used in Comparison example 4, except that the contact lens was not treated with polyvinyl alcohol, the physical properties were determined. The results are shown in Table 3.

Further, contact angles and stain resistance in the table were determined by the following method.

(I) Contact Angle

After contact lenses were subjected to hydrophilicity treatment and the surface was dried, the contact angle were determined by a water dropping method.

(II) Stain Resistance

After contact lenses were immersed in a physiological saline solution of 0.39% (w/v) of albumin, 0.17% (w/v) of lysozyme and 0.105% (w/v) of γ-globulin at a temperature of 35° C. for two weeks, the contact lenses were washed with physiological saline. Proteins sdhered on the contact lenses were peeled off with a surface-active agent, and a reagent for protein determination was injected into the protein solution. Then, the protein adsorption on the surface of the contact lenses was determined.

TABLE 3

| Example | Treating solution Preparation example | Contact lense | Solvent | Contact angle (%) | Stain resistance (μg/cm²) |
|---|---|---|---|---|---|
| 11 | 1 | HCL | EG | 51.9 | 3.7 |
| 12 | 1 | GPH | EG | 50.7 | 2.9 |
| 13 | 1 | SCL | EG | 46.8 | 2.8 |
| 14 | 2 | HCL | EG | 52.0 | 3.0 |
| 15 | 2 | GPH | EG | 53.9 | 3.9 |
| 16 | 2 | SCL | EG | 47.5 | 2.6 |
| 17 | 3 | HCL | EG/Water:50/50 | 49.3 | 4.7 |
| 18 | 3 | GPH | EG/Water:50/50 | 50.8 | 4.3 |
| 19 | 3 | SCL | EG/Water:50/50 | 44.8 | 4.0 |
| Comparison example | | | | | |
| 4 | PVA/Water | HCL | Water | 78.3 | 9.2 |
| 5 | | HCL | | 92.5 | 9.6 |

Note
HCL: Hard contact lens
GPH: Oxygen-Permeable hard contact lens
SCL: Soft contact lens
EG: Ethylene glycol
PVA: Polyvinyl alcohol.

We claim:

1. A process for cleaning contact lenses which comprises immersing contact lens in a solution comprising:

0.01–10% by weight of a copolymer obtained by copolymerization of 1–95% by weight of a monomer represented by the following general formula (1):

$$X-(Y)_n-O-\underset{\underset{O^-}{\overset{\overset{O}{\|}}{P}}}{}-O-(CH_2)_2-\underset{\underset{R_4}{|}}{\overset{\overset{R_2}{|}}{N^+}}-R_3$$

wherein X is $CH_2=\underset{R_1}{\overset{|}{C}}-CH_2-O$, $CH_2=\underset{R_1}{\overset{|}{C}}-CH_2-O-\underset{O}{\overset{\|}{C}}-$, $CH_2=\underset{R_1}{\overset{|}{C}}-O-\underset{O}{\overset{\|}{C}}-$, $CH_2=\underset{R_1}{\overset{|}{C}}-O-$, $CH_2=\underset{R_1}{\overset{|}{C}}-\underset{O}{\overset{\|}{C}}-O-$, $CH_2=\underset{R_1}{\overset{|}{C}}-\underset{O}{\overset{\|}{C}}-NH-$, $CH_2=\underset{R_1}{\overset{|}{C}}-CH_2-O-\underset{O}{\overset{\|}{C}}-NH-$, $CH_2=\underset{R_1}{\overset{|}{C}}-C_6H_4-CH_2-$, $CH_2=\underset{R_1}{\overset{|}{C}}-C_6H_4-O-$, $CH_2=\underset{R_1}{\overset{|}{C}}-C_6H_4-\underset{O}{\overset{\|}{C}}-O-$, and $R_1$ is hydrogen or methyl, Y is $-CH_2-$, $-CH_2-O-$, $-CH_2CH_2-O-$, $-CH_2CH_2CH_2-O-$, $-\underset{\underset{CH_3}{|}}{CHCH_2}-O-$, or $-CH_2CH_2CH_2CH_2-O-$;

n is an integer of 1–20, and $R_2$, $R_3$ and $R_4$ represent the same or different groups and are alkyl or hydroxyalkyl containing 1–8 carbon atoms, and 99–5% by weight of a copolymerizable monomer; and 90–99.99% by weight of a solvent containing ethylene glycol;

removing the lens from the solution; and then washing the lens with water.

2. The process for cleaning contact lenses according to claim 1, wherein the monomer represented by the formula (1) is one or more compounds selected from the group consisting of: 2-(methacryloyloxy) ethyl 2'-(trimethylammonio) ethyl phosphate, 3-(methacryloyloxy)propyl 2'-(trimethylammonio)ethyl phosphate, 4-(methacryloyloxy)butyl 2'-(trimethylammonio)ethyl phosphate, 5-(methacryloyloxy)pentyl 2,-(trimethylammonio)ethyl phosphate, 6-(methacryloyloxy) ethyl 2,-(trimethylammonio) ethyl phosphate, 2-(methacryloyloxy)ethyl 2'-(N-methyl-N,N-diethylammonio)ethyl phosphate, 2-(methacryloyloxy) ethyl 2'(N,N-dimethylethylammonio)ethyl phosphate, 2(methacryloyloxy)ethyl 2'-(triethylammonio)ethyl phosphate, 2(methacryloyloxy)ethyl 2'-(N,N-dimethylpropylammonio)ethyl phosphate, 2-(methacryloyloxy)ethyl 2'-(N,N-dipropyl-N-methylammonio)ethyl phosphate, 2-(methacryloyloxy)ethyl 2'(tributylammonio) ethyl phosphate, 2-(methacryloyloxy)ethyl 2'(tricyclohexylammonio)ethyl phosphate, 2- (vinyloxy) ethyl 2'(trimethylammonio)ethyl phosphate, 2- (allyloxy) 2'(trimethylammonio)ethyl phosphate, 2-(p-vinylbenzyl)ethyl 2'(trimethylammonio)ethyl phosphate, 2-(vinylbenzoyloxy)ethyl 2'(trimethylammonio)ethyl phosphate, 2-(styryloxy) ethyl 2'-(trimethylammonio) ethyl phosphate, 2(allyloxycarbonyl)ethyl 2'-(trimethylammonio)ethyl phosphate, 2-(vinyloxycarbonyl) ethyl 2'-(trimethylammonio)ethyl phosphate, 2-(acryloylamino)ethyl 2,-(trimethylammonio)ethyl phosphate, 2(allyloxycarbonylamino)ethyl 2'-(trimethylammonio)ethyl phosphate, (methacryloyloxy)methyloxy 2'(trimethylammonio)ethyl phosphate, 2-(methacryloyloxy)ethyloxy 2'-(trimethylammonio)ethyl phosphate, 3(methacryloyloxy)propyloxy 2'-(trimethylammonio)ethyl phosphate, 2-(methacryloyloxy) isopropyloxy 2'(trimethylammonio)ethyl phosphate, 4-(methacryloyloxy)butyloxy 2'-(trimethylammonio)ethyl phosphate, 2-(methacryloyloxy)propyl 2'-(trimethylammonio)ethyl phosphate, 2-(methacryloyloxy)butyl 2'-(trimethylammonio)ethyl phosphate, 2-(methacryloyloxy)ethyl 2'-(trimethylammonio)ethyl phosphate, 2-(methacryloyloxy)pentyl 2'-(trimethylammonio)ethyl phosphate, 2-(methacryloyloxy)hexyl 2'-(trimethy lammonio)ethyl phosphate, 2-(methacryloyloxy)ethyl 2'-(triphenylammonio)ethyl phosphate, 2-(methacryloyloxy) ethyl 2'-(trimethylammonio) ethyl phosphate, 2-(vinyloxy) ethyl 2'-(trimethylammonio) ethyl phosphate, 2-(allyloxy)ethyl 2'-(trimethylammonio)ethyl 2'(trimethylammonio)ethyl phosphate, 2- (p-vinylbenzyl) oxy 2'(trimethylammonio)ethyl phosphate, 2-(p-vinylbenzoyloxy)ethyl 2'-(trimethylammonio)ethyl phosphate, and 2-(p-vinylbenzyl)ethyl 2'-(trimethylammonio)ethyl phosphate.

3. The process for cleaning contact lenses according to claim 1, wherein the copolymerizable monomer is one or more compounds selected from the group consisting of styrene, methylstyrene, chloromethylstyrene, methyl (meth)acrylate, ethyl (meth) acrylate, n-butyl (meth) acrylate, (meth)acrylic acid, (meth)acrylamide, 2-hydroxyethyl (meth)acrylate, ethyl vinyl ether, n-butyl vinyl ether, N-vinyl pyrrolidone, vinyl chloride, vinylidene chloride, ethylene, propylene, isobutylene, and acrylonitrile.

4. The process for cleaning contact lenses according to claim 1, wherein the solvent also contains one or more compounds selected from the group consisting of water, methanol, isopropanol, polyethylene glycol, glycerine, ethylene glycol monomethyl ether, dimethyl sulfoxide, tetrahydrofuran, and acetone.

5. The process according to claim 1, wherein the cleaning solution is maintained at a temperature of 20° to 70° C. during immersion of the contact lens.

* * * * *